United States Patent [19]

Crovetti

[11] 4,092,433
[45] May 30, 1978

[54] QUINONE DERIVATIVES AS MOLLUSCICIDES

[75] Inventor: Aldo Joseph Crovetti, Lake Forest, Ill.

[73] Assignee: Abbott Laboratories, North Chicago, Ill.

[21] Appl. No.: 740,447

[22] Filed: Nov. 10, 1976

Related U.S. Application Data

[63] Continuation-in-part of Ser. No. 665,040, Mar. 8, 1976, abandoned, which is a continuation-in-part of Ser. No. 365,821, May 31, 1973, abandoned.

[51] Int. Cl.² ............................................. A01N 9/24
[52] U.S. Cl. .................................. 424/331; 424/244
[58] Field of Search ........................................ 424/331

[56] References Cited

U.S. PATENT DOCUMENTS

| | | | |
|---|---|---|---|
| 2,802,001 | 8/1957 | Marxer | 424/244 X |
| 2,976,279 | 3/1961 | Gauss et al. | 424/244 |
| 3,103,449 | 9/1963 | Lund | 424/33 X |
| 3,462,531 | 9/1969 | Jaques et al. | 424/244 X |
| 3,631,026 | 12/1971 | Nakao et al. | 424/244 X |

FOREIGN PATENT DOCUMENTS

| | | | |
|---|---|---|---|
| 951,045 | 4/1949 | France | 424/331 |
| 952,678 | 5/1949 | France | 424/331 |
| 1,417,385 | 10/1965 | France | 424/331 |
| 2,222,013 | 10/1974 | France | 424/331 |
| 43,838 | 4/1949 | Italy | 424/331 |
| 20,307 | 4/1971 | Japan | 424/331 |
| 2,310 | 9/1972 | Japan | 424/244 |

*Primary Examiner*—Dale R. Ore
*Attorney, Agent, or Firm*—Paul D. Burgauer; Robert L. Niblack

[57] ABSTRACT

Covers a method for the control of mollusks by treating said mollusk or its habitat with a compound of the formula:

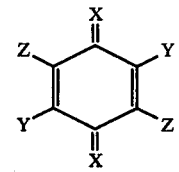

where Z is selected from the group consisting of hydrogen, halo and cyano; X is selected from the group consisting of

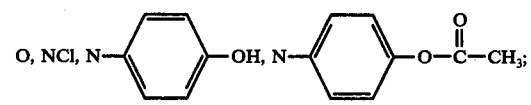

and Y is selected from the group consisting of halo, loweralkyl, aziridino, hydrogen, carboxyalkylthio, and cyano.

8 Claims, No Drawings

QUINONE DERIVATIVES AS MOLLUSCICIDES

CROSS-REFERENCE TO RELATED APPLICATION

This is a continuation-in-part of co-pending U.S. application, Ser. No. 665,040, filed Mar. 8, 1976, which is a continuation-in-part of U.S. application Ser. No. 365,821, filed May 31, 1973, both now abandoned.

DETAILED DESCRIPTION OF THE INVENTION

Many mollusks including snails and slugs, terrestrial as well as aquatic cause serious economic and health problems in many parts of the world. Snails which are members of a large class of gastropod mollusks including most forms having a univalve shell or having no shell can be quite injurious to vegatation as they destroy many varieties of beneficial agricultural plants. Even more harmful is the role that they play in the life cycle of many tropical and semitropical diseases. Millions of people and countless animals in many parts of the world are afflicted with these diseases. Snails play a significant role in the growth cycle of the parasite involved in these diseases. In the snails the parasite larval stages develop and emerge to enter warm-blooded animals and mature into worms. The worms in turn lay eggs which are carried to vital organs in the animal or human body by the bloodstream. Lastly, the eggs find their way back to the snails through water supplies and the like and the cycle beings once again. Thus, a single snail can be the ancestor of many millions of new snails per year.

For example, snails of the genre Oncomelania, Australorbis and Bulinus are schistosome intermediate hosts. Likewise, snails of the genre Lymnaea are intermediate hosts for the liver fluke worm. Snails of these genre particularly cause debilitating human problems. Specifically, bilharziasis has long been endemic in various parts of the world, and is even on the increase.

While various control methods of bilharziasis and other diseases of this type have been suggested, the destruction of intermediate snail hosts by toxic chemicals appears to be the most rapid and effective means for reducing transmission of many tropical and semitropical diseases.

However, many chemicals useful in combating mollusks such as snails, such chemicals generically termed as molluscicides, have certain disadvantages. In some cases they are difficult to formulate and in certain types of habitats available formulations do not disperse effectively. In other instances the chemical itself is irritating and potentially dangerous to the handler, is required for use at relatively high dosages, and may be prematurely used up by absorption by soil and organic material. Again, other molluscicides on the market are ineffective at a high pH, are corrosive to equipment or their activity is reduced by bright sunlight. Lastly, some molluscicides while sufficiently active are inactivated at a low pH and/or do not kill snail eggs.

In accordance with the invention, a new class of compounds useful as molluscicides have been discovered which exhibit activity against snails and related mollusks. Essentially the mollusks are controlled by subjecting them to the effect of a compound of the formula:

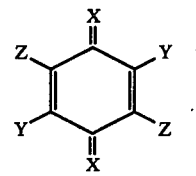

where Z is selected from the group consisting of hydrogen, halo and cyano; X is selected from the group consisting of

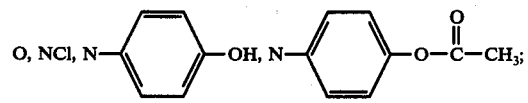

and Y is selected from the group consisting of halo, loweralkyl, aziridino, hydrogen, carboxyalkylthio, and cyano.

The term "loweralkyl" as used herein, refers to $C_1$-$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term "halo" includes chloro, fluoro, bromo and iodo.

Specific compounds falling within the above general structural formula which show particular efficacious utility in the area of mollusk control are as follows:

TABLE I

| Compound No. | Structure |
|---|---|
| 1 | ![structure] 2,5-dichloro-3,6-bis(aziridino)-1,4-benzoquinone |
| 2 | ![structure] 2,5-bis(aziridino)-1,4-benzoquinone |
| 3 | ![structure] tetrabromo-1,4-benzoquinone |
| 4 | ![structure] methyl-1,4-benzoquinone |
| 5 | ![structure] 2,5-bis(carboxyethylthio)-1,4-benzoquinone |

TABLE I-continued

| Compound No. | Structure |
|---|---|
| 6 | 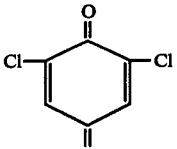 |
| 7 | 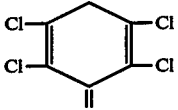 |
| 8 | 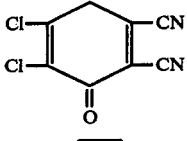 |
| 9 | 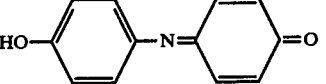 |
| 10 | 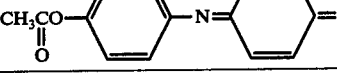 |

The above compounds were then screened for their molluscicide activity. Specifically, newly hatched snails of the strain B. glabrata numbering twenty were placed in well water at a temperature of 26° C. Test chemical was added to the well water in an amount to provide 10 ppm. After 24 hours' exposure to the chemicals the newly hatched snails were then examined for mortality rates. Table II below outlines results with regard to compounds 1 – 10.

TABLE II

| Compound No. | Mortality Rate |
|---|---|
| 1 | 20/20 |
| 2 | 20/20 |
| 3 | 10/20 |
| 4 | 20/20 |
| 5 | 20/20 |
| 6 | 14/20 |
| 7 | 20/20 |
| 8 | 20/20 |
| 9 | 20/20 |
| 10 | 20/20 |

One compound in particular showed highly active results as a molluscicide, and was subjected to further testing. Specifically 1,4-diaziridino benzoquinone was evaluated as a molluscicide utilizing adult snails of the B. glabrata strain. Ten snails were subjected to the chemical in each test sequence and inspected for mortality rates at various times. Table III below gives the results with regard to this particular chemical.

TABLE III

| | 1,4-Diaziridino Benzoquinone | | | |
|---|---|---|---|---|
| | Mortality Rate Time of Exposure | | | |
| Concentration (ppm) | 2 hrs. | 4 hrs. | 12 hrs. | 24 hrs. |
| 10 | 10/10 | 10/10 | 10/10 | 10/10 |
| 5 | 10/10 | 10/10 | 10/10 | 10/10 |
| 2.5 | 10/10 | 10/10 | 10/10 | 10/10 |

TABLE III-continued

| | 1,4-Diaziridino Benzoquinone | | | |
|---|---|---|---|---|
| | Mortality Rate Time of Exposure | | | |
| Concentration (ppm) | 2 hrs. | 4 hrs. | 12 hrs. | 24 hrs. |
| 1.0 | 0/10 | 3/10 | 10/10 | 10/10 |

In the above test a control after 24 hours showed a zero mortality rate.

The above compounds 1 – 10 and others falling within the general structural formula set out here are well-known materials and need little elaboration. They are prepared generally by reacting benzoquinone with an appropriate agent to yield the substitution on the benzoquinone ring, following by reaction in some cases of one of the oxygens of the benzoquinone structure to yield a compound having the requisite X radical.

As an example 1,4-diaziridino benzoquinone is prepared as follows: 50 gm. (0.25 mole) of cuprous acetate was slurried in 500 ml. of methanol. The resultant blue slurry was stirred at a temperature of 20° – 25° C. while adding 54 gm. of ethyleneimine (0.25 mole). The temperature was maintained by using an ice bath. Air was then bubbled through the blue solution and 27.0 gm. of p-benzoquinone in 1000 ml. of methanol (0.25 mole) was then added in a steady stream while maintaining the same temperature. After stirring for thirty minutes the resultant orange product was filtered off, washed with methanol and then water. The product was dried in an oven under a vacuum to yield a final product having a melting point of 208° – 210° C., dec. The theoretical product analysis calculated as: C: 63.15; H: 5.30

The analysis found was: C: 63.44; H: 5.03.

In practicing the present invention any of the various techniques or methods can be employed for exposing the mollusks to the toxic compounds above. For example, bait formulations can be prepared such that snails will seek out the treated bait. In application to a body of water for control of aquatic species, effective rates may be added directly thereto.

The benzoquinone compounds of the invention control aquatic mollusks when disseminated in the required concentration in the water in which the undesired mollusks are dwelling. Any suitable means for effecting the dissemination can be used—for example, formulations of the compounds can be stirred into the water, injected in a portion of the water wherein the water is in turbulent flow, or like mechanical means can be used. The dissemination can also be effected through the use of a highly hydrophilic surface-active agent, such as the water-soluble non-ionic surface-active agents, or water-soluble anionic surface-active agents.

This invention also provides novel molluscicidal compositions comprising a compound of the general formula hereinbefore specified, as the active ingredient or ingredients, together with a solid or liquid carrier or a surface-active agent, or a solid or liquid carrier and a surface active agent.

Aqueous dispersions in which the particles of said compounds are 5 microns or less in diameter, preferably less than 1 micron in diameter and more particularly of colloidal dimensions, exhibit molluscicidal activity. Such dispersions may be prepared by any suitable method known in the art. A particularly suitable method comprises pouring a concentrated solution comprising the compound and a dispersing agent in a water-miscible solvent into water, for example, into the water of the river, pond, irrigation canal, etc. to be treated. These solutions and the aqeous dispersions obtained on diluting them with water are compositions of the invention. The water-miscible solvent, may for example, be a water soluble aliphatic ketone such as acetone or methyl ethyl ketone, a water-soluble alcohol such as methyl, ethyl or isopropyl alcohol, dimethylformamide or ethyl oxitol. The dispersing agent suitably constitutes 5 to 20 percent by weight of the solution and preferably 5 to 10 percent by weight thereof. The dispersing agent used may be non-ionic, for example, polyalkylene oxide condensation products of alkylphenols such as the condensation product of octylphenol with 8 or 10 molecular proportions of ethylene oxide, or ionic, for example, sodium salts of secondary alkyl sulphuric acid esters containing 10 to 20 carbon atoms in the alkyl group, or sodium salts of sulphonates of alkyl aryl polyethers, or salts (particularly calcium salts) of alkyl aryl sulphonates such as calcium dodecylbenzene sulphonate. Mixtures of non-ionic and ionic dispersing agents may also be used.

The compositions of the invention may also be emulsifiable concentrates comprising a solution or dispersion of the compound in a water-immiscible organic liquid and an emulsifying agent. These compositions form more or less stable emulsions on addition to water. The water-immiscible organic liquid used may be, for example, a hydrocarbon for example, toluene, xylene, a mineral oil, for example, kerosine, or a petroleum horticultural spray oil or a chlorinated hydrocarbon, for example, a chlorinated benzene, carbon tetrachloride or trichloroethylene. The emulsifying agents may be of the types described above.

The compositions of the invention may also be wettable powders comprising the active benzoquinone in finely divided form and a dispersing agent such as lignin sulphonates or polyacrylates, or a dispersing agent and a wetting agent such as sodium lauryl sulphate, sodium N-methyl-N-oleyl taurate, sodium salts of petroleum sulphonates, sodium dioctyl sulphosuccinate, sulphonated esters of fatty alcohols, sodium salts of alkyl benzene sulphonates. A finely divided solid adsorbent carrier for example, adsorbent clay or synthetic silica, may be incorporated in the composition. If there is danger that the carrier employed may affect adversely the stability of the compound during storage of the wettable powder, it may be desirable to incorporate a stabilizing agent.

The compositions of the invention may also be in the form of granules, pellets or powders comprising the compound and a suitable carrier. These may be prepared by impregnating or treating an absorbent carrier including clay granules such as kaolin, attapulgite clays, with a solution of the compound or a mixture of the compound and a finely divided adsorbent carrier may be granulated or pelleted by methods well known in the arts. The compositions may also be prepared by dispersing the compounds in solid or liquid carriers, including water, alcohols, silica gel, and silicates such as calcium or sodium silicates, or sodium alumina silicate. The compounds may be mixed in solution and dispersed in these carriers by methods well known in the art. Alternatively, a resin carrier which is soluble in an organic solvent may be used, the compound being dissolved in the solution of the resin, the solvent then evaporated and the residue granulated. These compositions may be used against aquatic mollusks.

The concentration of the molluscicide to be used with the above carriers is dependent upon many factors, including the carrier employed, the method and conditions of application, and the snail or fish species to be controlled, a proper consideration and resolution of these factors being within the skill of those versed in the molluscicide art. In general, however, the compounds of this invention are effective in a concentration of from about 0.001 to 1.0% based upon the total weight of the composition, though under some circumstances as little as about 0.00001% or as much as 20.0% or even more (for example, up to 45%) of the compound can be employed with good results from a molluscicidal standpoint, as wherein high concentrations of active material are used in low-volume sprays or dusts.

The compositions of the invention may be used in conjunction with, or have incorporated in them, an attractant or bait for the mollusk.

The compound suitably constitutes 0.25 to 1 percent by weight of the attractant or bait though lower or higher concentrations may be used if desired.

The compositions of the invention containing no attractant or bait are preferably used so that when dispersed in water from 0.25 to 10.0 part by weight of the compound is present per million parts of water, though higher concentrations may be used if desired. At least about 0.1 part of the compound per million parts by weight of the water treated generally is required to effect control of aquatic snails within a reasonable time, and ordinarily not more than about 20 parts per million of the compound will be required. A fundamental advantage of the compositions comprising a bait in addition to the compound is that the compound content is not related to the volume of water to which the composition is applied.

The molluscicides of this invention can be employed alone, or in combination with other biologically active compounds, such as insecticides, fungicides, weed killers (particularly aquatic weed killers to destroy vegetation on which the snails can climb to avoid molluscicide in water), fertilizers, etc. These molluscicides are not merely specific against certain distinct mollusks, but will be effective against all snails and slugs, and mollusks generally, including, for example, species of Australoius, such as *A. quadelupensis*, species of Bulinus, such as *B. truncatus*, *B. angolensis* and *B. glabratus*, species of Tropicorpus, such as *T. centrimetralis*, species of Limnae, such as *L. natalensis*, *L. bulimoides*, and *L. auricularia*, species of Biophalaria, species of Galba, species of Oncomelania, species of Taphius, such as *T. glabratus*, *species of Helisoma such as H. trivolvis*, species of Marisa, such as *M. cornuarietis*, species of Pomacea, such as *P. lineata* and *P. glauca*, and species of Ocinebra, such as *O. japonica*.

I claim

1. A method for the control of mollusks which comprises treating a mollusk with an effective molluscicidal amount of a compound of the formula:

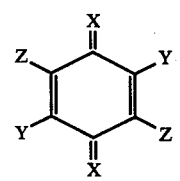

where Z is selected from the group consisting of hydrogen and halo; X is oxygen; and Y is selected from the group consisting of halo, loweralkyl and hydrogen.

2. The method of claim 1 wherein Z is chloro and Y is methyl.

3. The method of claim 1 wherein Z is hydrogen and Y is chloro.

4. The method of claim 1 wherein Z is bromo and Y is methyl.

5. The method of claim 1 wherein Z is hydrogen and Y is methyl.

6. The method of claim 1 wherein Z and Y are each chloro.

7. The method of claim 1 wherein Z and Y are each hydrogen.

8. The method of claim 1 wherein Z is chloro and Y is hydrogen.

* * * * *